(12) United States Patent
Mathiesen et al.

(10) Patent No.: US 7,328,064 B2
(45) Date of Patent: Feb. 5, 2008

(54) ELECTROPORATION DEVICE AND INJECTION APPARATUS

(75) Inventors: Iacob Mathiesen, Olso (NO); Torunn Tjelle, Olso (NO); Knut Arvid Sørensen Rekdahl, Tåmåsen (NO); Bjøm David-Andersen, Olso (NO)

(73) Assignee: Inovio AS, San Diego, CA (US)

( * ) Notice: Subject to any disclaimer, the term of this patent is extended or adjusted under 35 U.S.C. 154(b) by 513 days.

(21) Appl. No.: 10/612,304

(22) Filed: Jul. 3, 2003

(65) Prior Publication Data

US 2004/0059285 A1  Mar. 25, 2004

(30) Foreign Application Priority Data

Jul. 4, 2002 (GB) .................................. 0215523.2
Jul. 4, 2002 (GB) .................................. 0215529.9

(51) Int. Cl.
*A61N 1/30* (2006.01)
(52) U.S. Cl. ........................................................ 604/21
(58) Field of Classification Search ................ 604/117, 604/21, 20; 607/115, 116
See application file for complete search history.

(56) References Cited

U.S. PATENT DOCUMENTS

| | | | |
|---|---|---|---|
| 3,645,692 A | | 2/1972 | Stork et al. |
| 4,341,735 A | | 7/1982 | Seifried |
| 4,882,127 A | | 11/1989 | Rosenthal et al. |
| 5,271,413 A | * | 12/1993 | Dalamagas et al. ......... 600/547 |
| 5,273,525 A | * | 12/1993 | Hofmann ...................... 604/21 |
| 5,620,421 A | * | 4/1997 | Schmitz ...................... 604/135 |
| 5,672,317 A | | 9/1997 | Buhler et al. |
| 5,823,993 A | | 10/1998 | Lemelson |
| 5,993,434 A | * | 11/1999 | Dev et al. .................... 604/501 |
| 6,181,964 B1 | * | 1/2001 | Hofmann et al. ............. 604/21 |
| 6,208,893 B1 | * | 3/2001 | Hofmann ...................... 604/21 |
| 6,391,005 B1 | * | 5/2002 | Lum et al. .................... 604/117 |
| 6,418,341 B1 | * | 7/2002 | Hofmann et al. ............. 604/21 |
| 6,451,002 B1 | * | 9/2002 | Dev et al. .................... 604/500 |
| 6,706,016 B2 | * | 3/2004 | Cory et al. ................... 604/117 |
| 2003/0028172 A1 | * | 2/2003 | Epstein et al. ............... 604/507 |
| 2004/0260241 A1 | * | 12/2004 | Yamamoto et al. ......... 604/117 |

FOREIGN PATENT DOCUMENTS

| | | |
|---|---|---|
| EP | 0460650 A | 11/1991 |
| EP | 0 583 078 A2 | 2/1994 |
| EP | 0 693 951 B1 | 8/1998 |

(Continued)

OTHER PUBLICATIONS

International Search Report.

(Continued)

*Primary Examiner*—Sharon Kennedy
(74) *Attorney, Agent, or Firm*—Daniel M. Chambers; Douglas C. Murdock; BioTechnology Law Group

(57) ABSTRACT

An apparatus is provided for injecting a fluid into body tissue, the apparatus comprising:
 a hollow needle; and
 fluid delivery means,
wherein the apparatus is adapted to actuate the fluid delivery means in use so as to automatically inject fluid into body tissue during insertion of the needle into the said body tissue.

12 Claims, 17 Drawing Sheets

FOREIGN PATENT DOCUMENTS

WO      WO 98/43702      10/1998

OTHER PUBLICATIONS

Database WPI, Section Ch, Week 198736 Derwent Publications, Ltd., London, GB; Class B07, AN 1987-251781 XP002269622 & ES 8 706 023 A (Pascual J), Aug. 16, 1987 "Abstract".

Joshua R. Sanes et al., "Selective Expression of an Acetylcholine Receptor-IacZ Transgene in Synaptic Nuclei of Adult Muscle Fibers", Development 113, pp. 1181-1191 (1991).

Michael Chastain et al., "Antigen Levels and Antibody Titers after DNA Vaccination", Journal of Pharmaceutical Science, vol. 90, No. 4, Apr. 2001 pp. 474-484.

* cited by examiner

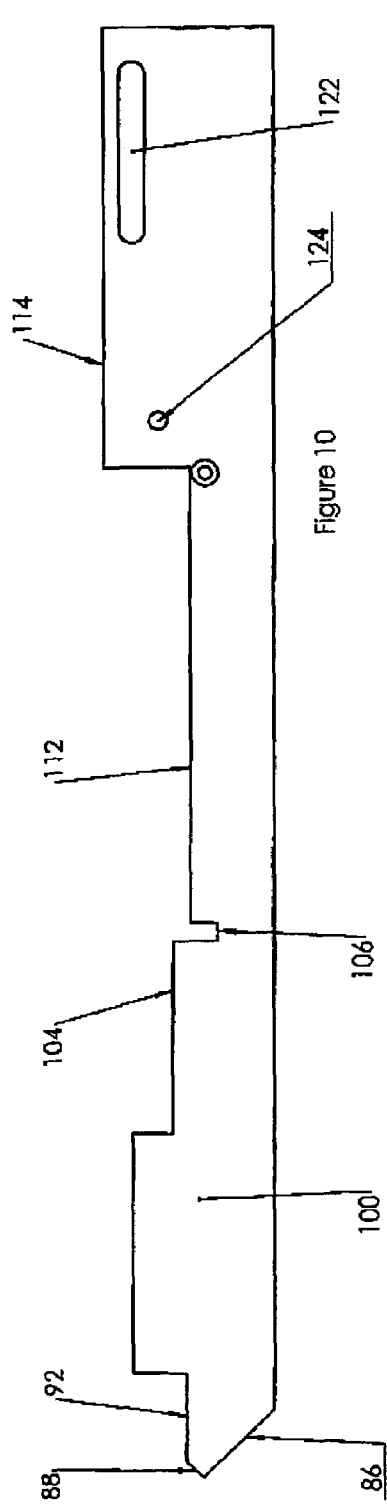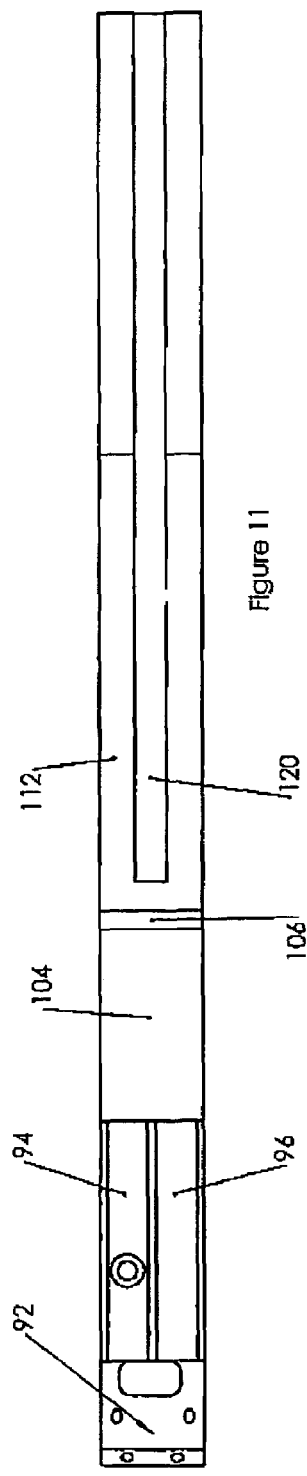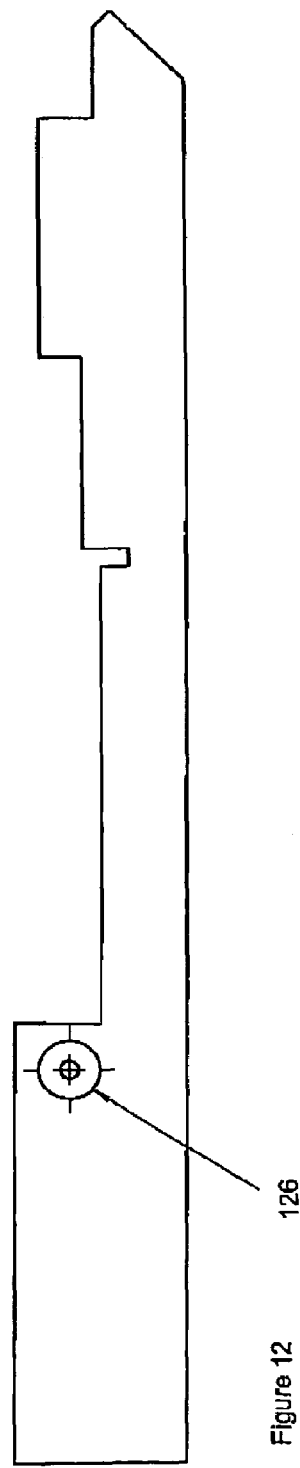

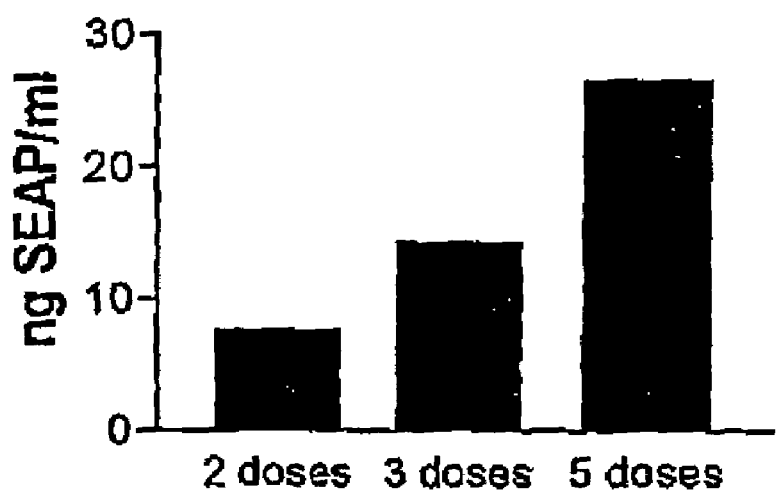
Figure 19
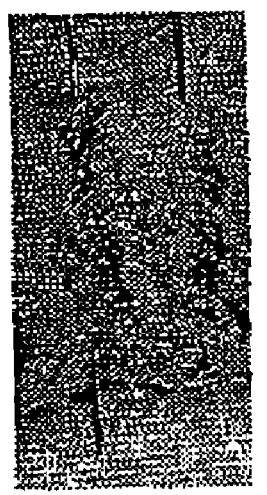 
Figure 20a					Figure 20b

ELECTROPORATION DEVICE AND INJECTION APPARATUS

The present invention relates to the injection of substances into tissue and, in one preferred application, to delivery by electroporation, i.e. the process of introducing substances into cells during or after the application of an electric field. More particularly, the present invention relates to a device which may be used in delivery by electroporation.

Electroporation is used for example in the treatment of cancer or in gene therapy. Electroporation provides a method of delivering pharmaceuticals or nucleic acids (e.g. DNA) into cells, e.g. skeletal muscle cells. Thus for example the muscle may be electrically stimulated at the same time or shortly after the pharmaceutical or DNA is injected. This method works on the principle that cells act as an electrical capacitor generally unable to pass current. Subjecting the cells to an electric field creates transient permeable structures or micropores in the cell membrane. The permeability or the pores are large enough to allow the pharmaceuticals and/or DNA to gain access to the cells. With time, the pores in the cell membrane close and the cell once again becomes impermeable.

Various devices for effecting electroporation have been suggested. U.S. Pat. No. 6,208,893 discloses an electrode template apparatus having a plurality of bores through which a plurality of needle electrodes extend, each bore being separately connected to a conductor so that each of the electrodes can be connected to a power supply in use. An insulating portion can be provided along the midportion of each electrode so as to isolate the body tissue adjacent the insulated part of the needle from the electric field produced by the electrode in use. Further, one or more of the needle electrodes may be hollow and can include openings through which medicinal substances can be injected into the body tissue.

EP0693951B discloses a device for the implementation of electrochemotherapy. The device comprises electrode needles through which electric pulses are applied. The electrode needles are hollow so as to allow active substances to be injected locally into the body tissue to be treated. Holes can be provided along the length of the needles as well as at the ends thereof to improve the distribution of injected substances. An insulating sheath can also be provided over a part of the needle lengths as a means of preventing the application of electrical pulses to certain zones.

The present invention at least in its preferred embodiments seeks to provide a device which can be used in electroporation in vivo, in particular in gene therapy.

One problem in electroporation is that DNA is injected intra-muscularly and may become trapped between muscle bundles or in adipose tissue between muscle cells. Further, the DNA can be stopped by tendons or other connective tissue barriers. This will make it difficult to obtain an even distribution of DNA over the entire area of tissue to which an electric field is to be applied. It is important to match the volume covered by the electric field applied during electroporation to the site of DNA injection to limit the distribution of the electrical field or volume of DNA. An additional problem is that when carried out on human beings, injections of large volumes of fluid at one site may cause considerable pain to the patient.

From a first aspect, the present invention provides an apparatus for injecting a fluid into body tissue, the apparatus comprising: a hollow needle; and fluid delivery means, wherein the apparatus is adapted to actuate the fluid delivery means in use so as to concurrently (preferably automatically) inject fluid into body tissue during insertion of the needle into the said body tissue. This has the advantage that the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection is preferably carried out after the needles have been inserted through the skin of the subject to be treated and while they are inserted further into the body tissue.

Suitable tissues into which fluid may be injected by the apparatus of the present invention include tumour tissue, skin or liver tissue but will preferably be muscle tissue.

Preferably the apparatus further comprises needle insertion means for guiding insertion of the needle into the body tissue. Still more preferably, the rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate.

If desired means for automatically inserting the needle into body tissue could be provided.

A user could choose when to commence injection of fluid. Ideally however, injection is commenced when the tip of the needle has reached muscle tissue and the apparatus preferably includes means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

In one preferred embodiment the sensing means comprises an ultrasound probe.

In an alternative preferred embodiment the sensing means comprises means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provide a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus preferably further comprises: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. Preferably therefore, the fluid delivery means comprise piston driving means adapted to inject fluid at a controlled rate.

The piston driving means could for example be activated by a servo motor. Preferably however, the piston driving means are actuated by the base being moved in the axial direction relative to the housing.

It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it preferably further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

As an aid to medical staff who may treat a large number of patients in a day, the apparatus may further comprise means for recording the identity of a subject to be treated and data from a treatment process.

Further, a fluid dispense vessel may be provided for use in the apparatus of the invention, in which a bar-code is provided on the vessel to identify the contents thereof. This barcode could be recognized by a pulse generator used in electroporation which would be programmed to automatically set up the required injection speed and electroporation conditions for the bar code.

From a further aspect, the present invention provides a method of injecting a fluid into body tissue, the method comprising: injecting the fluid into the body tissue through a hollow needle while the said needle is being inserted into the said body tissue. The injection of fluid gradually while the needle is being inserted leads to a more even distribution of the fluid through the body tissue. It is also believed that the pain experienced during injection is reduced due to the distribution of the volume of fluid being injected over a larger area.

Preferably, the needle tip is first inserted into the skin and injection is then carried out while the needle is inserted further into the body tissue.

Still more preferably, the injection is commenced when the needle reaches a first desired depth in the body tissue and is stopped when the needle reaches a second desired depth in the body tissue.

The method of injection described above may advantageously be used in conjunction with a method of electroporation wherein fluid is injected into body tissue by the method of injection of the invention and a voltage is then applied to the needle.

The method of injection described above may advantageously be used in conjunction with an alternative method of electroporation wherein fluid is injected into body tissue by the method of injection of the invention, the needle is withdrawn from the body tissue, an electrode is inserted in the place of the needle, and a voltage is applied to the electrode.

Gene therapy by electroporation involves administering a dose of between about 10 µL and 10 ml (e.g. between 10 µL and 1 ml, preferably between 100 µL and 1 ml) of DNA solution. DNA is toxic if too much is incorporated into cells and so the quantity of DNA in solution must not be too high. Thus, the quantities of solution are relatively small and, especially in larger animals such as human beings, it is difficult to administer both DNA and electric field to the right place in the muscle. Further, as the cells being treated should not be damaged, the electroporation device should be much gentler than the prior art devices whose primary use is in the treatment of cancer where the treated cells are killed. Ideally therefore, the electroporation device should not produce undue fields and should also not include any relatively blunt or bulky tissue pierces.

From a first aspect, the present invention provides an electroporation device comprising: a needle for injecting a substance into body tissue; and an insulating sheath adapted to surround the needle and having one or more apertures formed along the length thereof through which the electric field may propagate in use, wherein the needle is axially moveable relative to the sheath.

The device of the invention has the advantage that if the needle is also used as an electrode, as the needle is axially moveable relative to the sheath, the needle can be withdrawn so that the insulating sheath completely surrounds the needle after the device has been inserted into the body tissue and before the electric field generating means are activated. Thus in use, the electric field propagates through the apertures in the sheath, and so the formation of uneven electric field strengths in the body tissue to be treated is avoided as no edge effects are created.

Preferably, the needle for injecting a substance into body tissue also constitutes an electrode via which an electric field is propagated in use. Thus, in this preferred embodiment, the needle is connectable to a voltage source. It will of course be appreciated that, in one embodiment, the needle could remain connected to the voltage source at all times.

However if necessary, the device may be adapted to allow the needle to be removed from the insulating sheath after injection of the substance into the body tissue so that the needle can be replaced by an electrode rod prior to activation of the electric field. This would be advantageous for example to avoid the release of unwanted metal ions by the needle which could be caused by the provision of an electric charge on the needle. In this embodiment, the electrode rod would be arranged so as to be completely surrounded by the sheath in use so that again, no edge effects would be produced by the electric field in use.

The sheath could be formed of any electrically insulating and biologically compatible material. Preferably however, the sheath is formed from polytetrafluoroethylene (Teflon-$^{RTM}$).

Any number of apertures could be provided in the insulating sheath. In one preferred embodiment, the apertures are provided along one axially extending line on the sheath only. In an alternative preferred embodiment, the apertures are provided so as to be spaced around the circumference of the sheath. The actual number and arrangement of apertures provided in the sheath will depend on the electric field patterns required in the tissue to be treated.

The apertures in the insulating sheath could be formed in a number of ways such as but not limited to: cutting through the sheath, pushing the apertures out or laser ablation. Where apertures are required on one side only of the sheath, during aperture formation a rod can be provided within the sheath to prevent holes forming on both sides.

The electroporation device of the invention could be used alone. Preferably however, two or more electroporation devices are used together and if required, any number of the devices could be used Thus for example, a group of four, six or eight devices could be used. Where one or more devices are used, the needles and sheaths can be mounted to extend downwardly through a block in which they are arranged adjacent to one another. Consequently, it will be appreciated that any number of needles (i.e 1 or more could be used).

Preferably, means are provided such that in use the depth of insertion of a needle is determined and injection of a substance into the body tissue to be treated is commenced when the needle has reached a desired depth.

This is believed to be novel and inventive in its own right and so from a further aspect the present invention provides a device comprising a needle for injection of a substance into body tissue, and means for sensing the depth of insertion of the needle and commencing injection of a substance via the needle when a desired depth has been reached.

Various means could be provided to determine that the needle has reached a desired depth for injection to commence. For example, means for determining the electrical resistance of the tissue which will vary depending on tissue type (dermis, fat or tissue) could be provided. Preferably however, a moveable contact can be provided on the device such that in use, the contact determines when the needle has been inserted to a sufficient depth into the body tissue to be treated and then causes injection of a substance to commence. This allows automatic injection of a substance to commence when the needle reaches the correct depth in the body tissue to be treated. The injection can be carried out either while the needle is stationary or while it is continuing to be inserted.

Still more preferably, the moveable contact further determines when the needle has been inserted to the maximum depth at which injection should be carried out and then causes injection of the substance to stop. In this way it is possible for the substance to be automatically injected over the height of tissue over which an electric field will be produced in use.

Viewed from a further aspect the invention provides a method of electrophoretic treatment of a human or nonhuman animal (e.g. a mammal, bird or reptile), said method comprising inserting the needle of a device according to the invention into tissue (e.g. muscle tissue) in said animal, injecting an active agent (e.g. a pharmaceutical or nucleic acid) through the needle into the tissue, withdrawing the needle such that the tip thereof is within the sheath, and applying an electric field between the needle and an electrode.

It will be appreciated that the electrode could be provided by the needle of a second device according to the invention disposed inside a further sheath. Alternatively, the electrode could be a different type of electrode which had been inserted into the body tissue or an electrode which had been applied to the skin surface.

Viewed from a still further aspect the invention provides a method of electrophoretic treatment of a human or non-human animal (e.g. a mammal, bird or reptile), said method comprising inserting the needle of a device according to the invention into tissue (e.g. muscle tissue) in the animal, injecting an active agent (e.g. a pharmaceutical or nucleic acid) through the needle into the tissue, withdrawing the needle from the sheath, inserting a first electrode into the sheath such that the tip of the first electrode does not extend out of the sheath into the tissue, and applying an electric field between the first electrode and a second electrode.

It will be appreciated that the second electrode could be provided by the needle of a second device according to the invention disposed inside a sheath. Alternatively, the electrode could be a different type of electrode which had been inserted into the body tissue or an electrode which had been applied to the skin surface.

The device according to the invention could for example be used in the method of TWO98/43702, the contents of which are herein incorporated by reference. Preferably, the device would be used with a square bipolar electric pulse.

In the device of U.S. Pat. No. 6,208,893 as discussed above, the needle electrodes are inserted axially from above into the respective bores in use and are removed by being drawn axially outward after use. The present inventors have identified a problem with the use of such a device in which the bores become contaminated with the blood of an animal or person when the needles are withdrawn after use as the tips of the needles pass through the bores. Thus, the apparatus can only be reused after very thorough disinfection which is time consuming and expensive.

From a further aspect, the present invention seeks to provide a device which overcomes this problem. In a first aspect, the present invention provides a device for use in electroporation comprising a housing formed in two or more parts, wherein the parts are moveable relative to one another to open and close the housing, and a groove is formed in a surface of at least one of said parts in such a way as to form a bore extending through the housing when the housing is closed. Preferably the bore is adapted to receive a needle in use and the needle can be inserted and removed from the bore by opening the housing.

Thus, as the needle can be removed from the bore by opening the housing and so lifting it out of an open groove, there is no need to remove the needle from the bore by pulling it out in the axial direction Consequently blood and any other bodily fluids left on the tip of the needle after use need not be brought through the bore and so the housing will not be contaminated as in the prior art devices.

The parts of the housing could for example be held together in the closed position by a removable belt extending around the outside of the housing. Preferably however, the parts are hingedly attached to one another. This has the advantage of making the housing particularly easy to open and close.

The housing could for example be formed in four parts which make up the quarters of a cuboid, each part having a groove with the cross section of a quadrant formed at the inner corner thereof. Alternatively, the housing could be formed in two parts, with a groove having for example a semi-circular or square cross section formed on the inner surface of one part while the surface of the other part is flat. Preferably however the housing is formed of two parts, a groove of semicircular cross section being provided on the inner surface of each part and being positioned to form a bore of circular section from the two grooves when the housing is closed. It will be appreciated that in this arrangement, the parts of the housing can be hingedly attached together at one end thereof in a manner allowing simple manufacture and use of the device. Further, the circular cross section of the bore is particularly advantageous as the needles to be held therein are normally circular in cross section.

Still more preferably, the housing is formed to receive two needles in two respective bores. Although the device could be used with any number of needles, two needles are often required to carry out electroporation and so this is a particularly preferred arrangement.

The needles could be connected to an electric power supply by standard means such as cables attached to an end of the needle extending out of the housing. Preferably however an electrical contact is provided for or within the or each bore so that a needle within the bore is brought into contact with an electrical power supply when the housing is closed. This has the advantage that a user need not spend time connecting a needle to a power supply by attaching cables etc. and so is much quicker and simpler to use.

Still more preferably, the device is configured so as to lock the needle in position within the bore when the housing is closed in use. Thus, no additional means need be provided to stop the needle from moving relative to the housing during insertion of the needle into the body tissue to be treated and the subsequent electroporation process.

In one preferred embodiment, a foot pedal could be provided to activate the power supply when required for electroporation. This has the advantage that a user would have their hands free at all times to hold the device and the needle(s) in place in an animal or person being treated. It will be appreciated however that alternative means such as a switch provided on the needle holder could be provided for activating and deactivating the power supply.

The device of the invention could be used with any standard known, approved needles and injection assemblies or syringes.

In one preferred embodiment, the device could be used with one or more needles, wherein each said needle is surrounded by an insulating sheath, the sheath having one or more apertures formed along the length thereof. The use of such insulated needles has the advantage of reducing the production of edge effects when the needle is used as an electrode.

Preferably, the same needle is used for injecting a substance into the body tissue to be treated and applying an electric field. Where necessary however, the needle could be withdrawn front the sheath arranged within a bore of the housing after injection of a substance into the body tissue to be treated and substituted by an electrode rod for carrying out the electroporation. This would be advantageous for example to avoid the release of unwanted metal ions by the needle which could be caused by the provision of an electric charge on the needle. In this embodiment, the electrode rod could be arranged to be completely surrounded by an insulating sheath to avoid the production of edge effects by the electric field in use. Further, the insulating sheath arranged within the bore would protect the bore from contamination by blood and/or other bodily fluids as the needle was withdrawn axially from within the bore and sheath.

Preferably, even if the needle is not completely withdrawn from the sheath after injection of a substance into the body tissue, the needle is still axially moveable relative to the sheath. This allows the needle to be withdrawn inside the sheath after injection so that it is fully surrounded by the sheath before the application of an electric field. This has the advantage of further reducing the production of edge effects by the electric field in use.

The sheath could be formed of any electrically insulating and biologically compatible material. Preferably however, the sheath is formed from polytetrafluoroethylene (Teflon-$^{RTM}$).

Preferably, the needles used for injection of a substance into the body tissue to be treated are attached to syringe devices via which injection is carried out. It would also be possible however for the needles to be provided separately for attachment to injection means at an appropriate time.

Preferably, the device is provided with means for determining the depth of insertion of a needle into the body tissue to be treated in use and for automatically commencing injection of a substance into the body tissue to be treated when a desired depth of the needle has been reached.

Preferably a moveable contact can be provided on the device such that in use, the contact determines when the needle has been inserted to a sufficient depth into the body tissue to be treated and then causes injection of a substance to commence. This allows automatic injection of a substance to commence when the needle reaches the correct depth in the body tissue to be treated. The injection can be carried out either while the needle is stationary or while it is continuing to be inserted.

Still more preferably, the moveable contact further determines when the needle has been inserted to the maximum depth at which injection should be carried out and then causes injection of the substance to stop. In this way it is possible for the substance to be automatically and accurately injected over the height of tissue over which an electric field will be produced in use.

Viewed from a further aspect, the present invention provides a method of electroporation treatment of a human or non-human animal (e.g. a mammal, bird or reptile), said method comprising inserting a needle held in a device according to the invention into tissue (e.g. muscle tissue) in said animal, injecting an active agent (e.g. a pharmaceutical or nucleic acid) through the needle into the tissue, applying an electric field between the needle and an electrode, removing the needle from the tissue and opening the housing of the device to remove the needle therefrom.

Preferably, the needle could be pushed further into the tissue after injection and before the application of an electric field to enable the electric field to be applied over the full height of injected fluid.

It will be appreciated that the electrode could be provided by a second needle held in a or the device according to the invention. Alternatively, the electrode could be a different type of electrode which had been inserted into the body tissue or an electrode which had been applied to the skin surface.

It will further be appreciated that the needle could be any known approved form of needle or any other type of needle described herein.

In an alternative preferred method of treatment, the needle is removed from the device according to the invention after injection and replaced by an electrode, an electric field being applied between the two electrodes before the electrode is removed.

The device according to the invention could for example be used in the method of TWO 98/43702, the contents of which are herein incorporated by reference. Preferably, the device would be used in an electroporation method in which a square unit or bipolar electric pulse is applied to the electrode.

From a further aspect, the present invention provides a method of determining when a needle has been inserted to a desired depth in body tissue comprising measuring a change in impedance as the needle is inserted into the body tissue.

Although this could be achieved in various ways, two needles are preferably inserted into the body tissue adjacent one another and the impedance between the needles is measured.

Preferred embodiments of the invention will now be described, by way of example only, and with reference to the accompanying drawings in which:

FIG. 10 is a side elevational view of the base of the device of FIG. 7;

FIG. 11 is a top plan view of the base of the device of FIG. 7;

FIG. 12 is a side elevational view of the base of the device of FIG. 7 from the opposite side to that shown in FIG. 10;

FIG. 19 shows the amount of SEAP used in serum in a test using a device according to the invention; and FIGS. 20a and 20b shows the results of the test using a beta-galactosidase expressing vector introduced using a device according to the invention.

Figure 1:
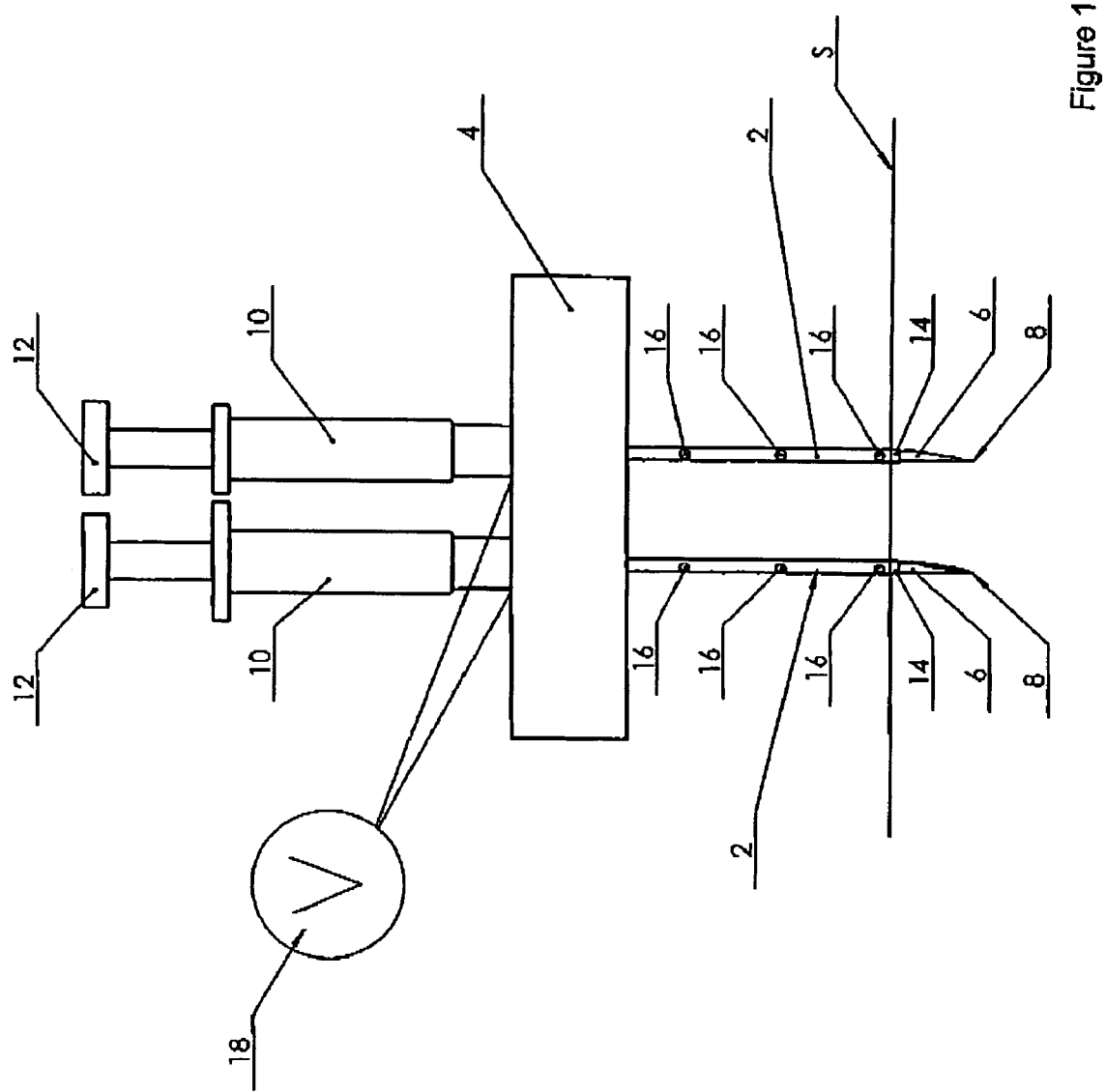
FIG. 1 is a schematic side elevation view of an electroporation device according to a first embodiment of the invention.

As shown in FIG. 1, an electroporation device according to a first embodiment of the invention comprises two separate needle assemblies 2 mounted adjacent to one another in a support block 4. Each needle assembly 2 comprises a hollow needle 6 having a sharp end 8 which is open to allow the injection of fluids via the opening. The other end of each of the needles 6 is connected to a fluid holding chamber 10 having a piston 12 arranged therein so as to form a syringe arrangement for injecting fluid via the needles in use. These syringes may be standard single-use syringes.

First and second electrically insulating sheaths 14 made of Teflon$^{RTM}$ and having a greater cross sectional diameter than that of the needles 6 are arranged to extend around the needles 6. Three apertures 16 spaced apart in the axial direction are provided along the length of each sheath 14. The device is configured so as to allow axial movement of the needles 6 relative to the sheaths 14.

A voltage supply 18 is provided on the support block 4 which can be connected and disconnected from the needles 6 of the electroporation device.

In use, a required dose of DNA (which could for example be 100 μL) is provided in each of the fluid holding chambers 10 and the needles 6 are inserted into the skin of an animal or person to be treated. It is advantageous that the volume of fluid for injection should be small as this will insure that the injected fluid is kept close to the shaft of the needle (i.e. will be kept within a high electric field strength zone during electroporation). At this stage, the sharp ends 8 of the needles 6 extend beyond the Teflon sheaths 14 and so provide a sharp point for piercing the skin and penetrating into the muscle or body tissue to be treated. During insertion, the relative position of the needles 6, sheaths 14 and support block 4 does not vary as the elements are locked into place relative to one another. The needles are then inserted further until they reach the correct depth in the muscle or other body tissue to be treated. Once they have reached this depth and while still being inserted, the DNA is injected into the muscle by pushing downwardly on the pistons 12 to empty the fluid holding chambers 10. If necessary, the needles can then be pushed further down into the muscle after injection. This ensures that the needles acting as electrodes cover the area into which the fluid has been injected.

After insertion of the needles and once the DNA has been injected, the needles 6 are withdrawn slightly (i.e. moved axially towards the support block 4) relative to the Teflon sheaths 14 which remain in their original inserted position. Thus, the sharp ends 8 of the needles 6 are retracted to locate within the Teflon sheaths 14. Once the needles 6 have been retracted as described, the voltage source 18 is activated and electroporation proceeds with each of the needles 6 acting as an electrode. The electric field produced by the needles 6 acting as electrodes propagates into the muscle or body tissue to be treated via the apertures 16 formed along the length of the Teflon shields 14. This has the advantage that no unwanted edge effects are created in the muscle or body tissue to be treated.

Figure 2C:
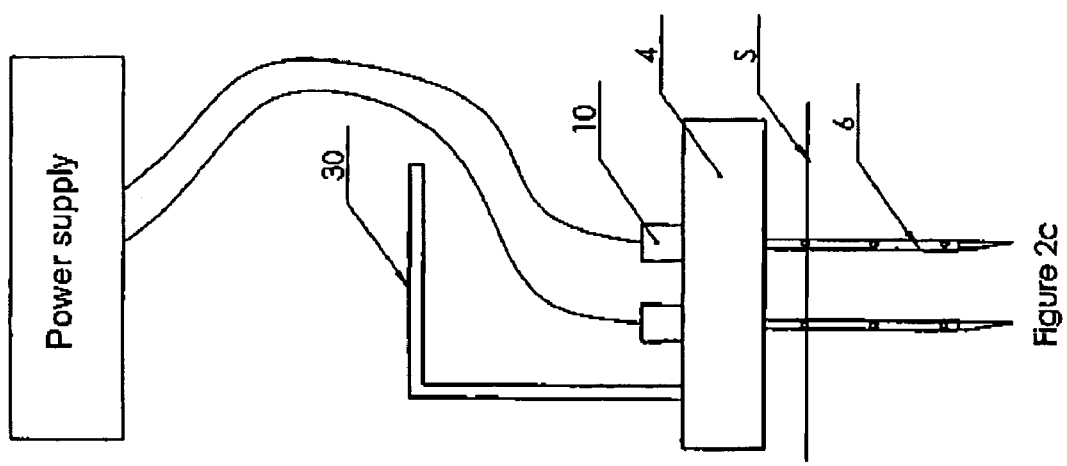
FIGS. 2a to 2c are schematic side elevation views showing three stages in the operation of an electroporation device according to the first embodiment of the invention including a skin contact device.
Figure 2B:
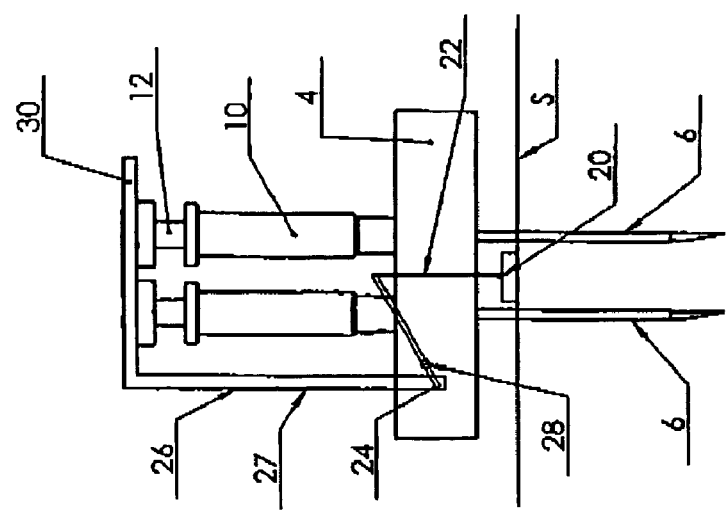
Figure 2A:
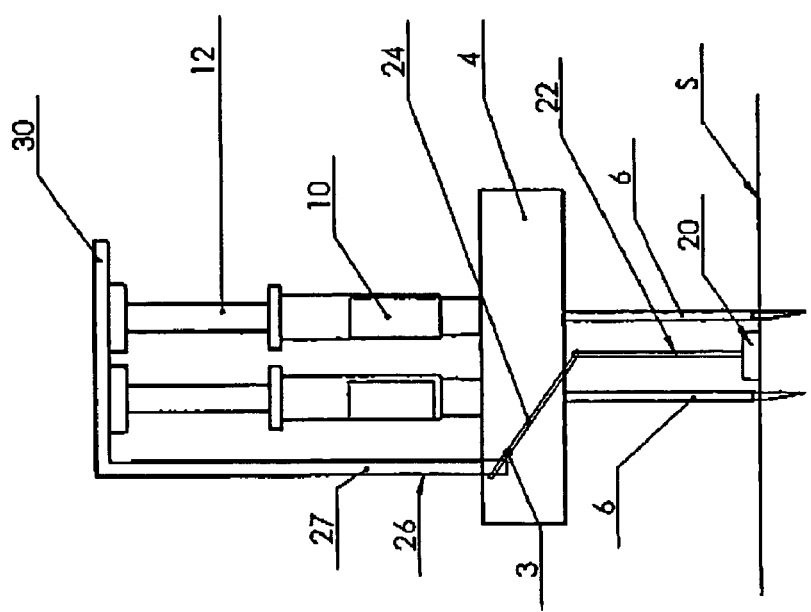

In a further improvement to the device of FIG. 1 (as shown in FIGS. 2a to 2c), means are provided to sense when during insertion the needles 6 are at the correct depth in the muscle or body tissue for injection of the DNA to begin and to automatically move the pistons 12 to effect the injection. These means comprise a moveable skin contact 20 which contacts the skin S as shown in FIGS. 2a to c. As the needles 6 are inserted into the muscle or body tissue to be treated, the contact 20 is pushed upwardly towards the support member 4. The contact member 20 is attached to a lever mechanism consisting of a substantially vertical link 22 extending upwardly from the contact member 20 and a lever 24 which is attached at a first end to the vertical link 22. The lever 24 is attached at its other end to means 26 for causing the pistons 12 to move downwardly. The lever is adapted to pivot about a point 28 on the support member 4 located between the two ends of the lever 24. Thus, as the contact 20 moves upwardly relative to the support member 4 in use, the lever 24 pivots causing the piston moving means 26 to push the pistons down gradually so as to effect injection of the fluids over the height of the needles being inserted. As shown, the piston moving means comprise a vertical member 27 attached to the lever 24 so as to move downwardly as the lever pivots and a cross piece 30 attached to the other end of vertical member 27 which acts to push the pistons down as it moves downwardly with the vertical member.

The relative location of the skin contact 20 and lever mechanism can be adjusted to ensure injection of the fluids once the needles have reached the muscle tissue and while they are being inserted further into the tissue to ensure a uniform distribution of sample in the area around the electrodes in the muscle.

FIG. 2a shows the device before the pistons have been pushed down with the tips of the needles just inserted into the skin. FIG. 2b shows the device when the needles are fully inserted to the required depth in the muscle tissue and the pistons 12 have been fully depressed by the action of the lever mechanism. FIG. 2c shows the device once the needles have been attached to a power supply 18 after injection of the fluids. As shown, the syringes have been removed although this is not essential.

In alternative embodiments, lasers or sensors could be used to detect the depth of insertion of the needles and automatically initiate injection of the fluids at a desired depth instead of the mechanical skin contact arrangement described above.

The contact or sensors can be further adapted to sense when the needles 6 have reached a depth in the body tissue at which injection of the fluids should stop so as to ensure that fluid is only injected into the height of body tissue to which an electric field will be applied in use.

It will be appreciated that one advantage of the embodiment of the invention described above is that known cannula devices which are already on the market and so have marketing approval can be used to provide the needle and sheath assemblies of the device, the only modification which is required being the formation of the apertures 16 in the sheaths. Thus, the use of such commercially available cannulas can ensure rapid and inexpensive regulatory clearance. One example of a known cannula device which could be used is the 0.8/25 mm diameter Venflon$^{RTM}$ sold by BOC Ohmeda AS of Helsingborg, Sweden.

In an alternative embodiment of the invention (not shown) the needles 6 can be withdrawn from the muscle or body tissue to be treated after the DNA has been injected into it and electrodes having a similar shape but made of an alternative metal such as stainless steel can be inserted before electroporation is carried out. This could be useful for example in a situation where biologically incompatible metal ions would be emitted if the needles 6 were also used as the electrodes.

Figure 3:
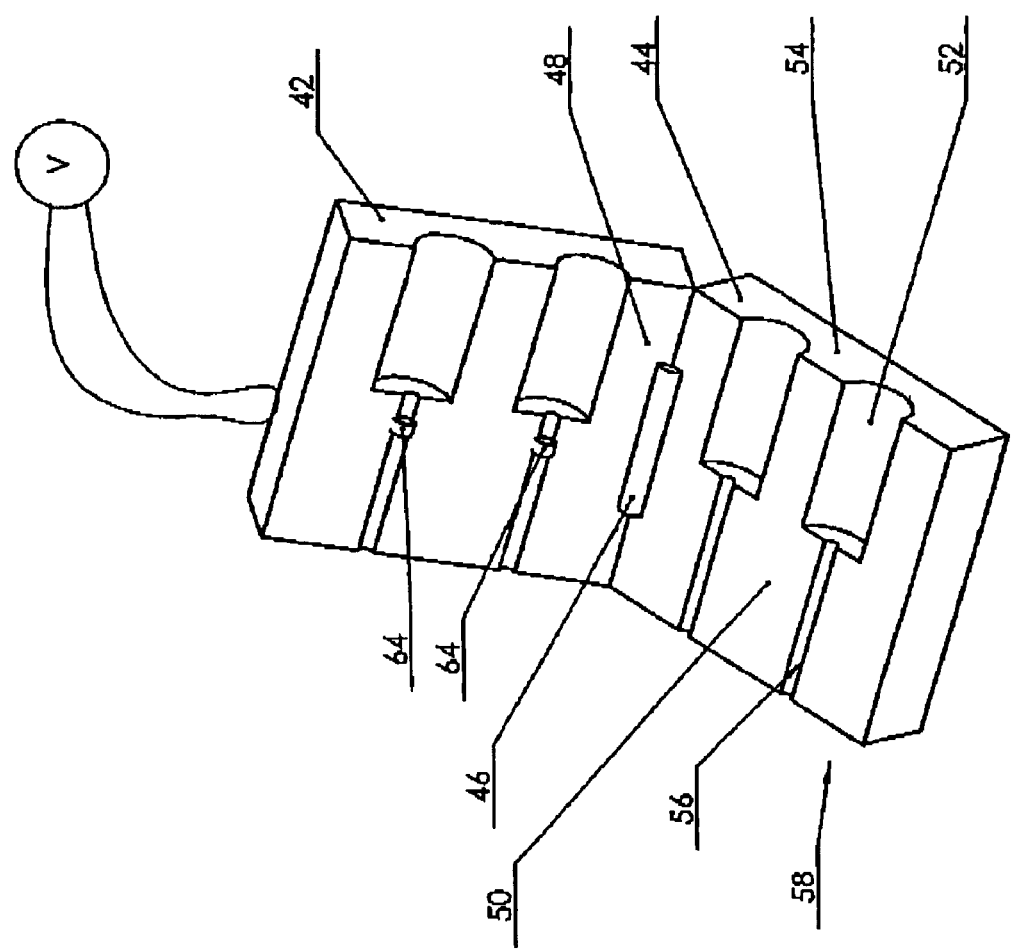
FIG. 3 is a perspective view of an electroporation device according to a second embodiment of the invention in an open position.
Figure 4:
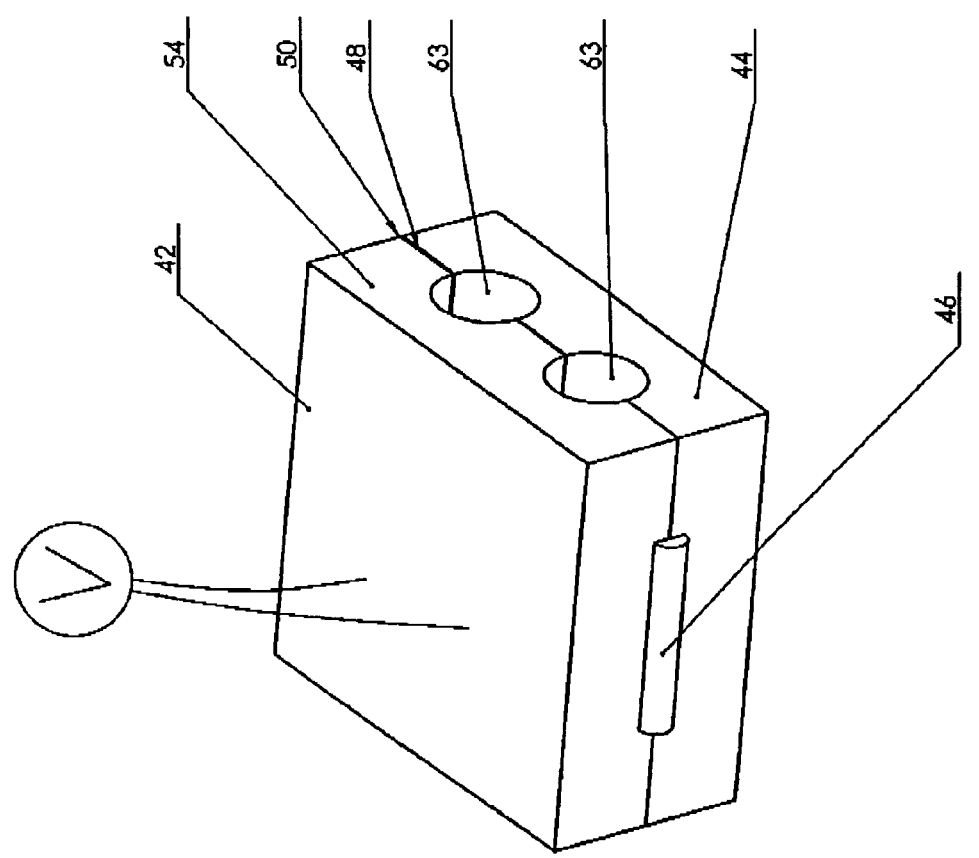
FIG. 4 is a perspective view of the device of FIG. 3 in the closed position.

As shown in FIG. 3, a device according to a second embodiment of the invention comprises a housing 41 made up of two halves 42, 44 which are joined together by a hinge 46 Each half 42, 44 of the housing is a rectangular solid and the hinge 46 is provided between adjacent end faces thereof so that the upper plane rectangular surfaces of each half of the housing can be pivoted towards each other until the upper surface 48 of the first half 42 lies directly above the upper surface 50 of the second half 44. In this position, the housing is said to be closed and this is shown in FIG. 4.

Figure 5:
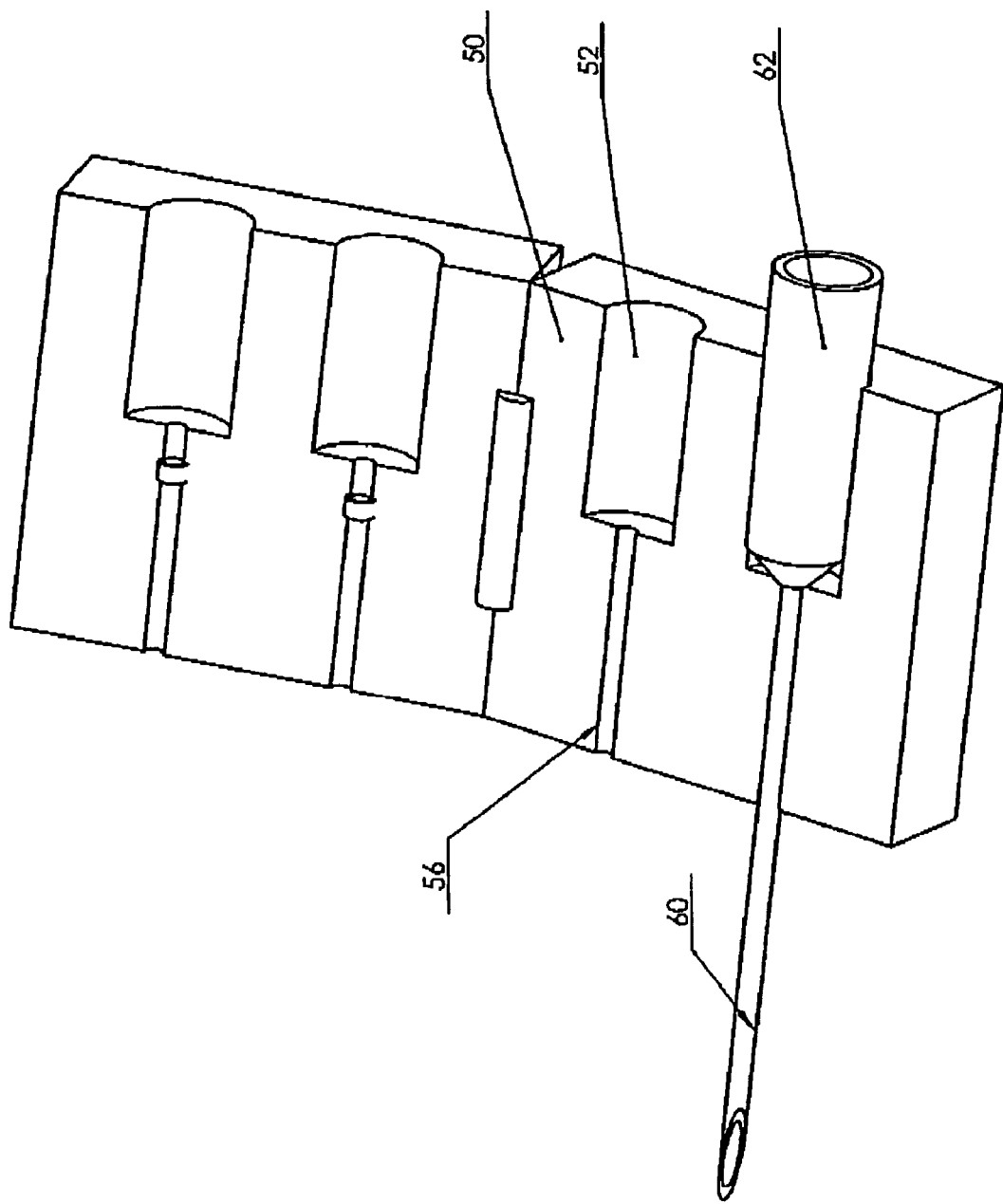
FIG. 5 is a schematic plan view of a part of the device of FIG. 3 holding a needle and injection device.

From FIG. 3, it can be seen that recesses or grooves are formed in the upper surfaces 48, 50 of each of the two halves 42, 44. Each groove is semi-circular in cross section and has a wider portion 52 extending from a first side 54 of the housing half which leads into a narrower portion 56 which extends to the other side 58 of the housing half. Thus, in use the needle 60 of a syringe device fits into the narrower portion 56 while the syringe or injection part 62 adjacent the needle fits into the wider portion 52 as shown in FIG. 5.

The upper surface 48 of the first half 42 of the housing 41 has two recesses of the type described above formed therein which are laterally spaced from one another. Two recesses are also formed in the upper surface 50 of the second half 44 at corresponding locations such that, when the housing is closed so that the first 48 and second 50 surfaces are arranged one above the other, the recesses in the first and second surfaces join to form two bores 63 within which respective needles and syringe or injection devices may be held.

Also as shown in FIG. 3, an electrical contact element 64 is provided in the narrower part 56 of each recess in the first half 42 of the housing. The electrical contact elements 64 are connected to an electrical power source V and arranged so that a needle placed within the recess will automatically be brought into contact with the electrical contact element when the housing is closed.

The device shown and described with reference to FIGS. 3 and 4 can be used with any standard approved needle and syringe device such as for example the Sterile EO CE0123, Sterican 0.40×40 mm BL/LB, 27G×1½.

Figure 6:
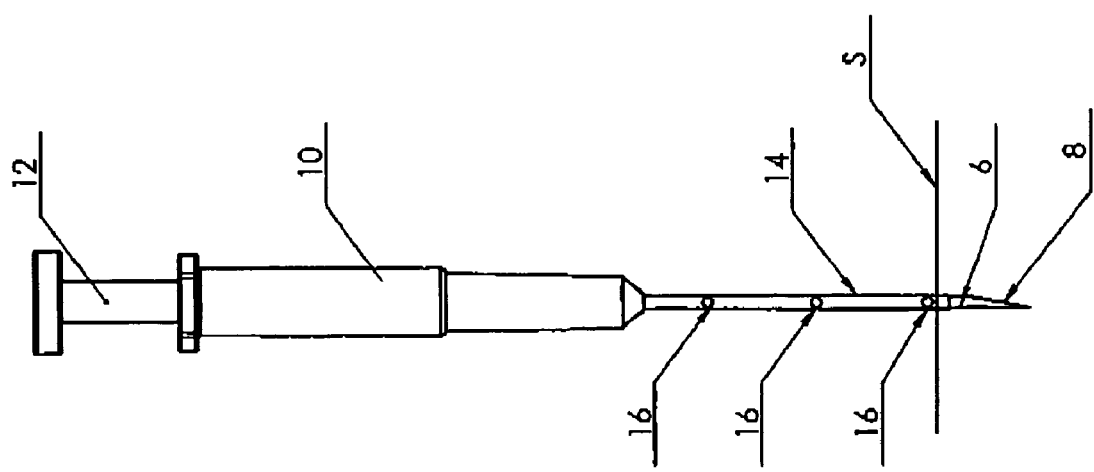
FIG. 6 is a schematic elevational view of an alternative needle and injection device for use with the device of FIG. 3.

In an alternative embodiment, the device can be used with syringe devices including needles 6 which are surrounded by insulating sheaths 14 such as those shown in FIG. 1 for use with the device of the first embodiment of the invention. A syringe device of this type for use in the second embodiment of the invention is shown in FIG. 6. As can be seen, the device includes a needle 6 and a Teflon$^{RTM}$ sheath 14. As shown in FIG. 6, the insulating sheath 14 which surrounds the needle has three apertures 16 spaced apart from one another in the axial direction and provided along the length of the sheath. A fluid container 10 including a piston 12 is provided at one end of the needle for injecting fluid therethrough. In one embodiment, the needle is axially moveable relative to the sheath so that after it has been inserted into the body tissue to be treated, the needle is withdrawn into the sheath. This avoids the formation of harmful edge effects when an electric field is applied to the needle. Known cannula devices which are already on the market and so have marketing approval can be used to provide the needle and sheath assemblies of the device, the only modification which is required being the formation of the apertures 16 in the sheaths. Thus, the use of such commercially available cannulas can ensure rapid and inexpensive regulatory clearance. One example of a known cannula device which could be used is the 0.8/25 mm diameter Venflon$^{RTM}$ sold by BOC Ohmeda AB of Helsingborg, Sweden.

If desired, means may be provided with the device of the second embodiment of the invention to sense when the needles 6, 60 are at the correct depth in the muscle or body tissue for injection of the DNA to begin and to automatically move the pistons 12 to effect the injection in the same way as for the first embodiment of the invention as shown in FIGS. 2a to 2c. When used with the device of the second embodiment however, the lever 24 pivots about point 28 on the housing 41 rather than support block 4.

A method of electroporation treatment using the device of FIGS. 3 and 4 will now be described. This method could be carried out on any human or non-human animal. A required dose of DNA (which could for example be 100 μl) is provided in each fluid container 12, 62. Then the syringe devices are inserted into respective recesses 52, 56 in one half 42 of the housing 41 and the housing is closed so that the needles are held firmly in place in the respective bores formed by the recesses. The needles are then inserted into the body tissue as shown at FIG. 2*a*. The needles are pushed down to the correct depth for injection of the DNA and this is then carried out. After the injection, the needles are then pushed slightly further down into the body tissue and the electric power supply V is activated by a foot pedal (not shown) to apply an electric field via the needles.

After the electric field has been applied, the needles are removed from the body tissue and the housing is opened so that the needles can be lifted out of the recesses. The housing is then ready to be reused with new needles.

Figure 7:
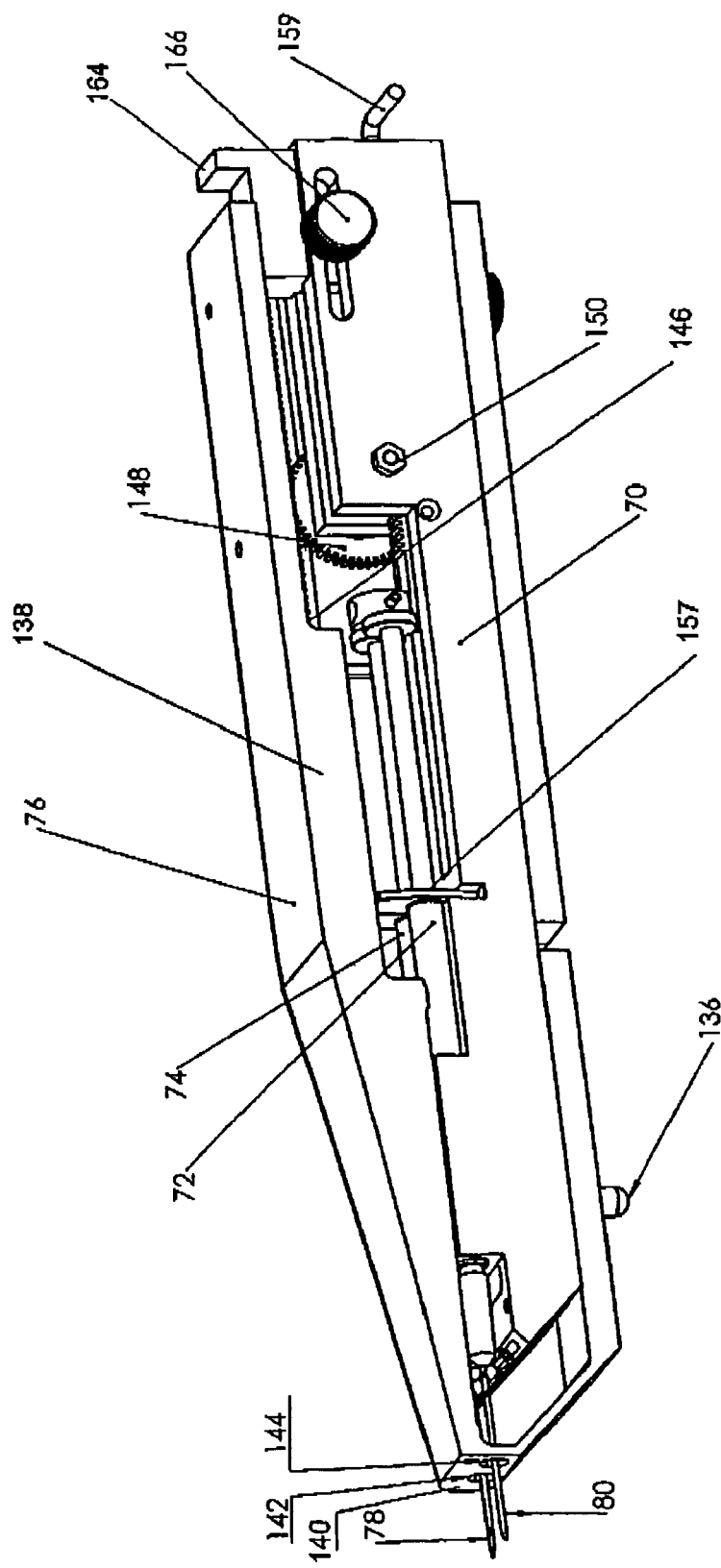
FIG. 7 is a side perspective view of an electroporation device according to a third embodiment of the invention.
Figure 8:
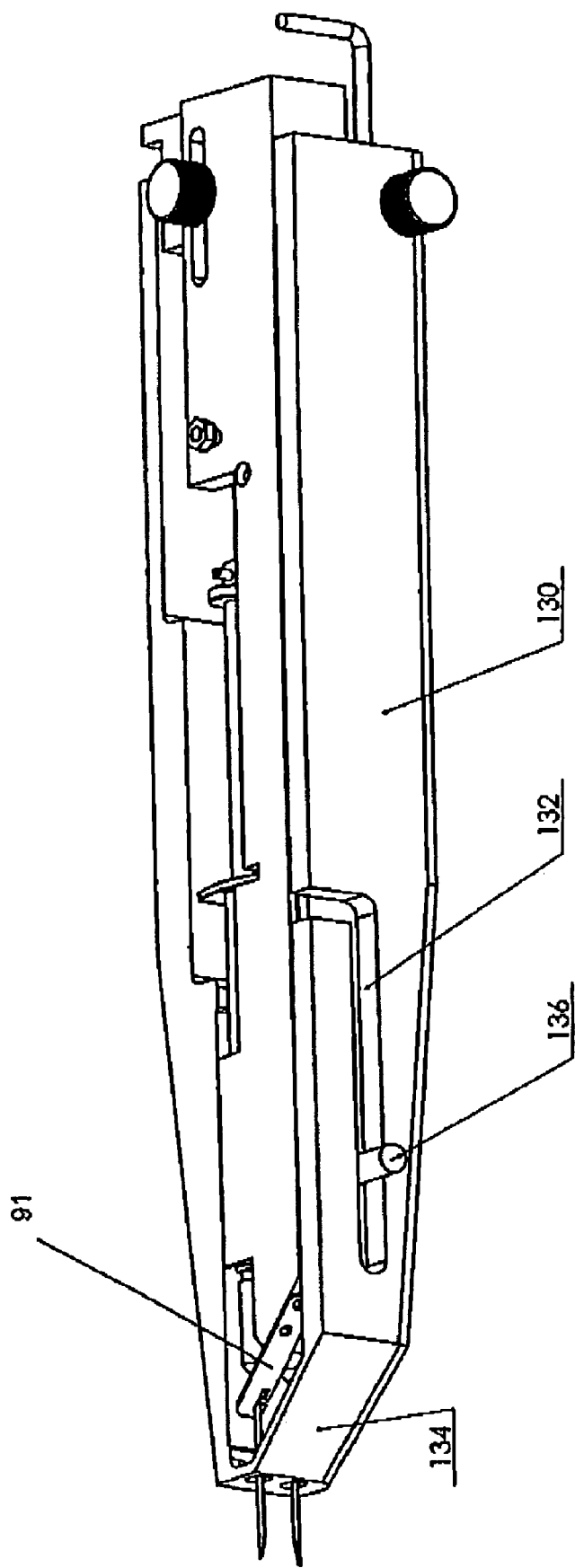
FIG. 8 is an underneath perspective view of the device of FIG. 7.

A third and most preferred embodiment of the invention will now be described with reference to FIGS. 7 to 13. As shown in FIG. 7, the device comprises a base 70 which holds two syringe devices 72, 74 and a cover 76. The base 70 is capable of sliding relative to the cover 76. This motion simultaneously inserts both the needles 78, 80 of the syringe devices and drives a gear mechanism (see FIG. 16) to cause injection of fluid via the needles. This will be described in greater detail below.

Figure 9:
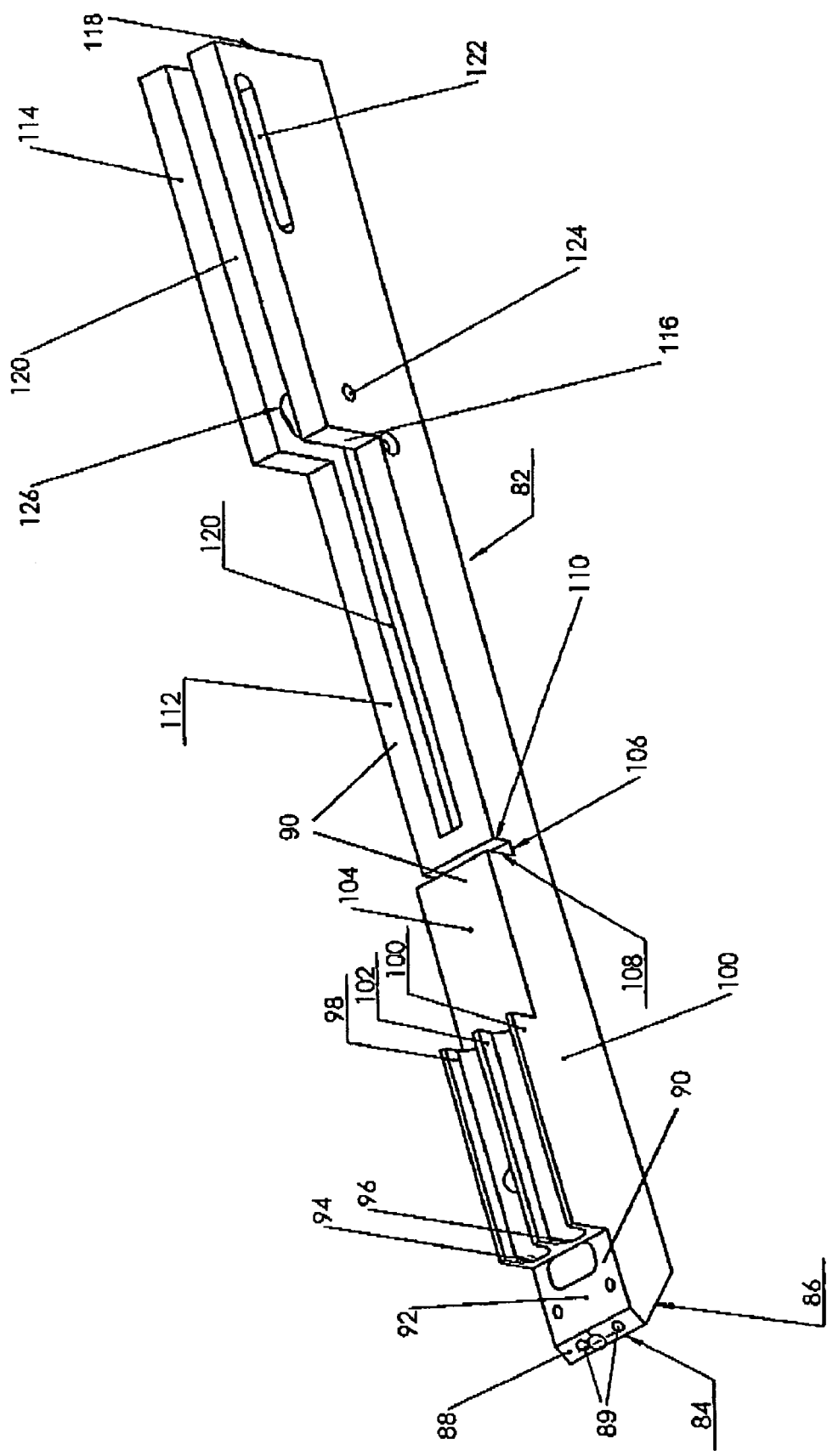
FIG. 9 is a side perspective view of the base of the device of FIG. 7.
Figure 13:
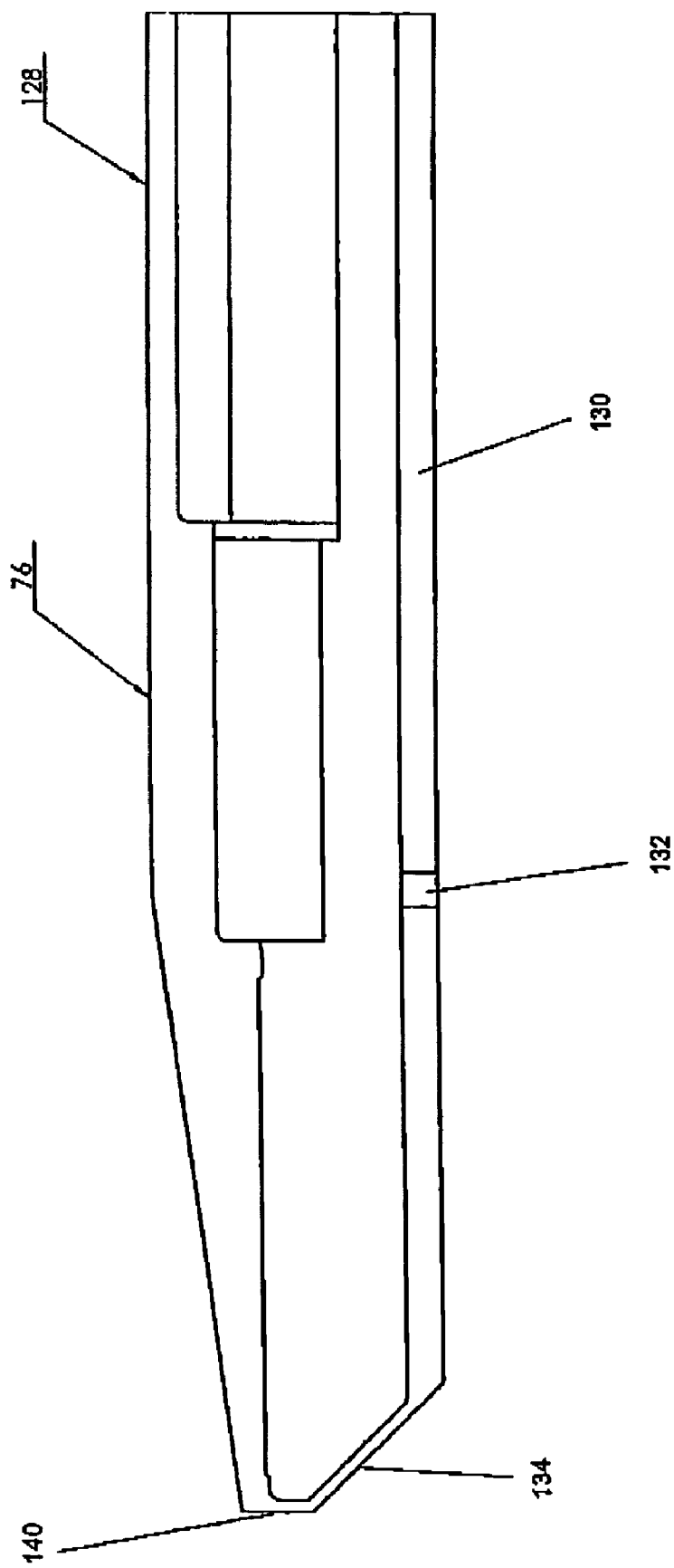
FIG. 13 is a cross sectional side view of the cover of the device of FIG. 7.

The base 70 is shown in FIG. 9. It is formed from plastic (for example polyvinyl chloride) although it could also be produced in other suitable materials such as stainless steel (or mouldable plastics). The base 70 has a long solid body which is substantially rectangular in plan view. A bottom surface 82 thereof is substantially flat and is adapted to rest slidably on an inner surface of the cover 76. A first end 84 of the base 70 is adapted to slide forwardly into engagement with the cover 76 and so comprises a contact surface 86 extending upwardly at an acute angle (45° in the embodiment shown) from an end of bottom surface 82. A chamfer 88 is provided between the angled contact surface 86 and the upper surface 90 of the base 70.

The upper surface 90 of the base 70 is adapted to receive syringe devices 72, 74. The first part 92 of the upper surface 90 extends rearwardly from chamfer 88 to form a first planar surface which is parallel to bottom surface 82 and extends a short distance (preferably about 16 mm or about 6% of the total length of the base 70) rearwardly of the chamfer 88 end. Contacts 91 for providing electrical power to each needle are provided on the base, and power may be supplied to these via wires connected to any standard plug and socket arrangement. The contacts also form a stability arrangement 91 for holding and supporting the needles during electroporation.

The combined contact and stability arrangement 91 is provided by two hooked metal plates attached to the angled contact surface 86. The hooked metal plates are electrically connected to wires (not shown) which may supply electrical power from any suitable power supply via the above-mentioned pulg and socket arrangement (not shown). Furthermore, at chamfer 88, springs 89 are provided, the springs also being electrically connected to the above-mentioned wires. The springs 89 serve to press the needles 78 and 80 against their respective contacts 91, thereby ensuring electrical connection.

Beyond first part 92, a pair of parallel syringe holding grooves 94, 96 extending in the direction of the longitudinal extent of base 70 are provided. The grooves 94, 96 have external side walls which are coplanar with and form part of the side walls 96, 100 of base 70 and have a central wall 102 separating the two grooves. The external side walls and central wall have straight sides and extend above the level of first part 92 of upper surface 90 (preferably by about 9 mm). Further the grooves 94, 96 are formed with semi-circular bases having a radius of curvature of 3.3 mm and the lowest part of the grooves is located above the first part 92 of upper surface 90 (preferably by about 2 mm). The grooves 94, 96 extend over a distance of about 2 to 3 times the length of first part 92 of upper surface 90 (preferably over about 16% of the total length of the base or about 41 mm).

Rearwardly of the parallel syringe holding grooves 94, 96, a second planar surface 104 extends parallel with the bottom surface 82 and on the same level as the lowest part of grooves 94, 96. The second planar surface has a similar length to the parallel syringe holding grooves 94, 96 (and preferably extends over about 13% of the total length of the base or about 33 mm).

Rearwardly of the second planar surface 104, a notch 106 is cut out of the base 70 extending across the base (i.e. perpendicular to the longitudinal extent thereof). The notch 106 has straight side edges 108, 110 and is cut out to a level below the second planar surface 104 (preferably by about 7.5 mm). The notch preferably has a dimension of about 3 mm in the longitudinal extent of the base 70).

At the side of notch 106 facing away from the second planar surface 104, a third planar surface 112 extending parallel to the bottom surface 82 is provided at a level above the base of notch 106 but below second planar surface 104. (The third planar surface 112 is preferably at a level about 3 mm below second planar surface 104). The third planar surface 112 preferably extends over about 31 of the total length of the base or over a distance of about 79 mm.

Immediately rearwardly of the third planar surface 112 a fourth planar surface 114 extends parallel to the bottom surface 82 and above the third planar surface (preferably about 14.3 mm above the third planar surface). A straight edge 116 extending perpendicular to the longitudinal direction joins the third and fourth planar surfaces to each other.

The second end 118 of the base 70 comprises a planar surface extending perpendicular to the longitudinal extent and joining the fourth planar surface 114 to the bottom surface 82.

A groove 120 with straight edges is cut out from the upper surface 90 of the body of the base 70, the groove extending longitudinally along the center of the base from the second end 118 thereof to a point within the third planar surface 112 close to the notch 106 The groove 120 has a flat bottom which is about 4 mm below the level of the third planar surface 112. The groove is about 4.1 mm wide.

An aperture 122 is cut through one side of the base 70 underneath the fourth planar surface 114 to the groove 120 to form a longitudinally extending guide in which a pin may slide. The aperture is preferably 4.2 mm high and about 29 mm long, is centered about 4.7 mm below the fourth planar surface 114 and extends from about 8 mm from the second end 118 of the base 70.

A circular aperture 124 is cut through the base 70 to the groove 120 and is located on the same side of the base 70 as aperture 122 underneath the fourth planar surface 114. The aperture 124 is centered on a point about 8 mm from the straight edge 116 joining the third 112 and fourth 114 planar surfaces arid about 5.3 mm below the fourth planar surface 114. The aperture 124 has a diameter of about 3 mm.

A second circular aperture 126 is cut through the base 70 on the other side from and centered on the same point as the circular aperture 124. The second circular aperture 126 has a diameter of about 10 mm.

Figure 18:
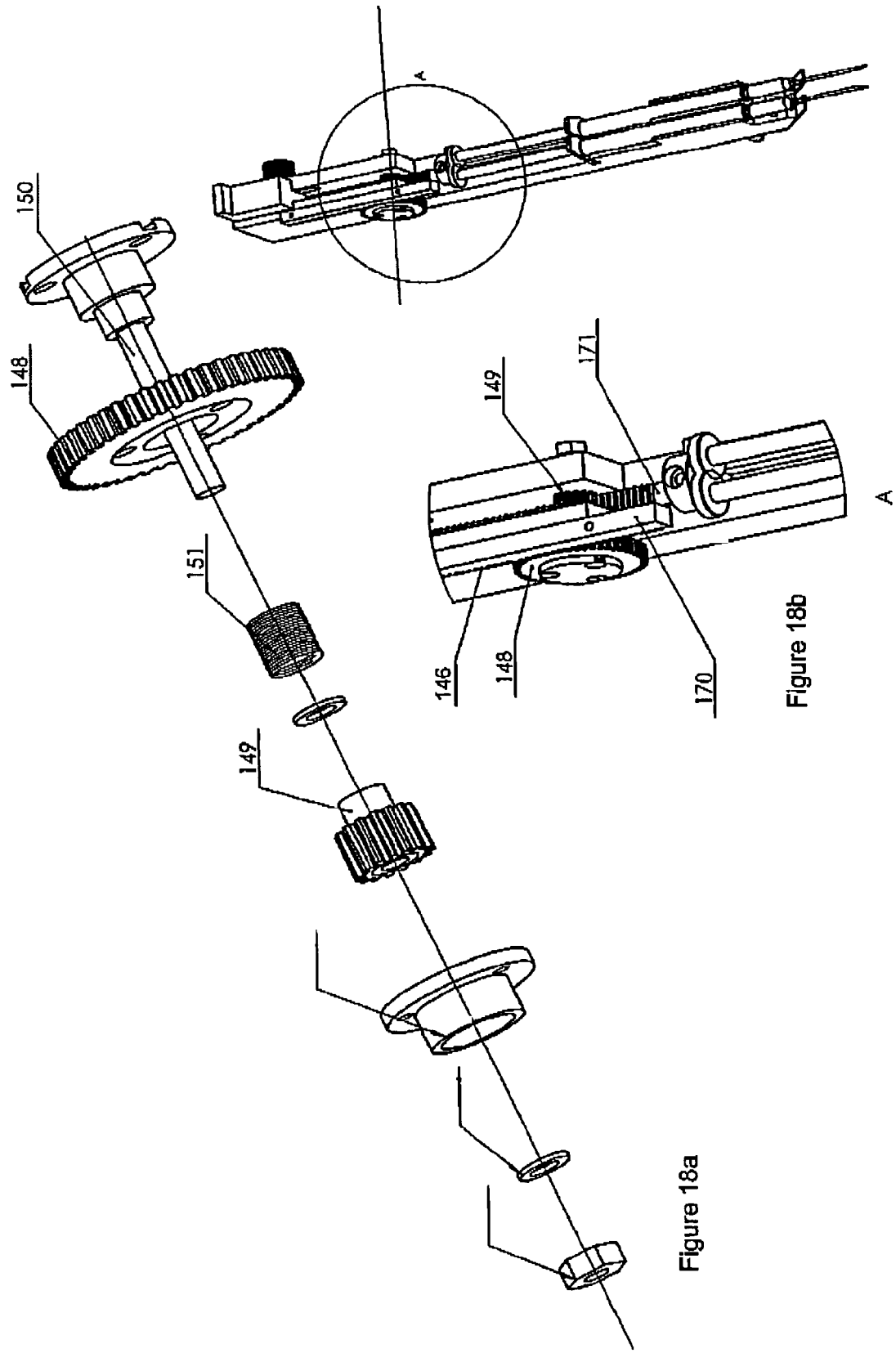
FIG. 18a is an exploded view of the gear mechanism of the device of FIG. 7 for driving the needle insertion and injection process.
FIG. 18b is a view of the gear mechanism of FIG. 18a mounted on the base unit.
FIG. 18c is a view of the base unit showing the gear mechanism of FIG. 18a and the rack member in place.

A gear wheel 148 on an axle 150 is mounted externally of the base 70 by passing the axle through the first circular aperture 124 and then through the second circular aperture 126 and securing the axle using a nut on the other side of the base 70. In use, the base is moved forwardly relative to the cover and the gear wheel 148 engages on a rack 146 provided on toothed member 170, or on a toothed track provided on the cover to cause the gear wheel 148 to rotate. The gear wheel is adapted to engage with a smaller gear wheel 149 also mounted on the axle 150 which drives injection of fluid from the two syringes mounted on the base by a further gear-rack mechanism 171. As shown in FIG. 18*a*, a spring 151 is mounted on the axle 150 between the large gear wheel 148 and the smaller gear wheel 149. The spring 151 enables a one-way gear mechanism by virtue of which large gear 148 drives small gear wheel 149 when rotating in a first direction but does not drive the small gear wheel when rotating in the opposite direction. This will be described in further detail below.

A lever, 159 is provided on base 70 at the end 118 thereof which can be pulled out from the base to shorten the length by which the needles can project beyond base 70.

As stated above, the base 70 is adapted to be received within a cover 76 as shown in FIG. 7. The cover 76 is shown in greater detail in the cross sectional side view of FIG. 13. The cover is again a solid body which could for example be made of polyvinyl chloride.

The cover 76 has a first side wall 128 shaped to cover substantially all of the base 70. The side of the cover opposite the first side wall 128 is open to allow access to the base 70 when it is mounted in the cover. A first end 134 of the cover is shaped to cooperate with the first end 86 of the base 70, i.e. it extends upwardly at an acute angle (45° in the embodiment shown) away from the bottom of the cover. The opposite end of the cover is open such that the base 70 projects beyond the open end when inserted in the cover in use.

On the bottom of the cover 76 extending outwardly from the first side wall 128 is a planar support surface 130 which extends across the full length and width of the cover so as to receive the bottom surface of the base thereon. An L-shaped guide groove 132 is provided in the support surface 130 extending from the open side of the cover across the support surface perpendicular to the longitudinal direction approximately to the center of the support surface and then extending in the longitudinal direction towards the first end of the cover. This guide groove 132 is adapted to receive a pin 136 attached to the bottom surface 82 of base 70 in use and a user moves the base forwards and backwards relative to the cover by manually moving this pin 136 in the groove 132. The pin 136 and guide groove 132 arrangement has the advantage that the base cannot fall out of the cover in use.

Further supports which hold the base 70 in place within the cover 76 in use are provided projecting from the first side wall 128 to the other side of the cover. These supports project both over the first end of the cover and along the top or upper edge thereof (forming parts 134 and 138 respectively). These are dimensioned so that gaps are left between the upper support 138 of the cover and various parts of the base 70 in use. A flat portion 140 extends perpendicular to the longitudinal extent of the cover between the sloping part of the first end 134 and the upper edge 138 of the cover. This flat portion is provided to be easily placed on the skin of a subject for injection and two apertures 142, 144 are formed through it to allow two needles supported adjacent one another above the base 70 to pass through the cover for insertion.

A toothed track 146 is provided on the upper support 138 to engage with the gear wheel 148 mounted on base 70 in use.

A stopping member 164 including a projection for engaging with the open end of cover 76 is mounted on base 70 by a screw 166 engaging in the longitudinal aperture 122. The distance that the base can move within the cover (and hence the maximum achievable depth of needle insertion in use) can be adjusted by moving the stopping member 164 relative to the base 70 by sliding the screw 166 in the aperture 122. The longitudinal aperture 122 may be provided with a scale to indicate the maximum depth of needle insertion enabled at respective positions of screw 166. Alternatively, the scale could be provided on the base 70 itself to be read off against a point on the stopping member 164.

In use, the base 70 and cover 76 are separated. The gear wheel 148 is then pushed right back on the toothed track or rack 146 until it disengages therefrom. This enables the later placement of full syringes into the base without any fluid being spilled. Either one or both syringes are then filled with fluid (this depending on the treatment desired). The two syringes 72 and 74 having barrels 152, 154 are the mounted in base 70 such that the needle ends 156, 158 extend beyond the end of the base and the ends of their piston rods 160, 162 abut against a pushing mechanism 171 driven by the small gear wheel 149.

One of the two syringes contains DNA or another substance for injection into the person or animal to be treated. The other syringe may be empty and be used solely to act as an electrode during the subsequent electroporation process or it may be full of DNA or other fluid for injection in the same manner as the first syringe. The syringes are held against axial movement relative to the base 70 by annular projections 157 provided on the syringes which are received in the notch 106 in base 70 in use. The syringes are held against movement in the direction perpendicular to the axial direction by the grooved 96, 98 which extend upwardly on either side of each syringe when fitted in the base.

Figure 14:
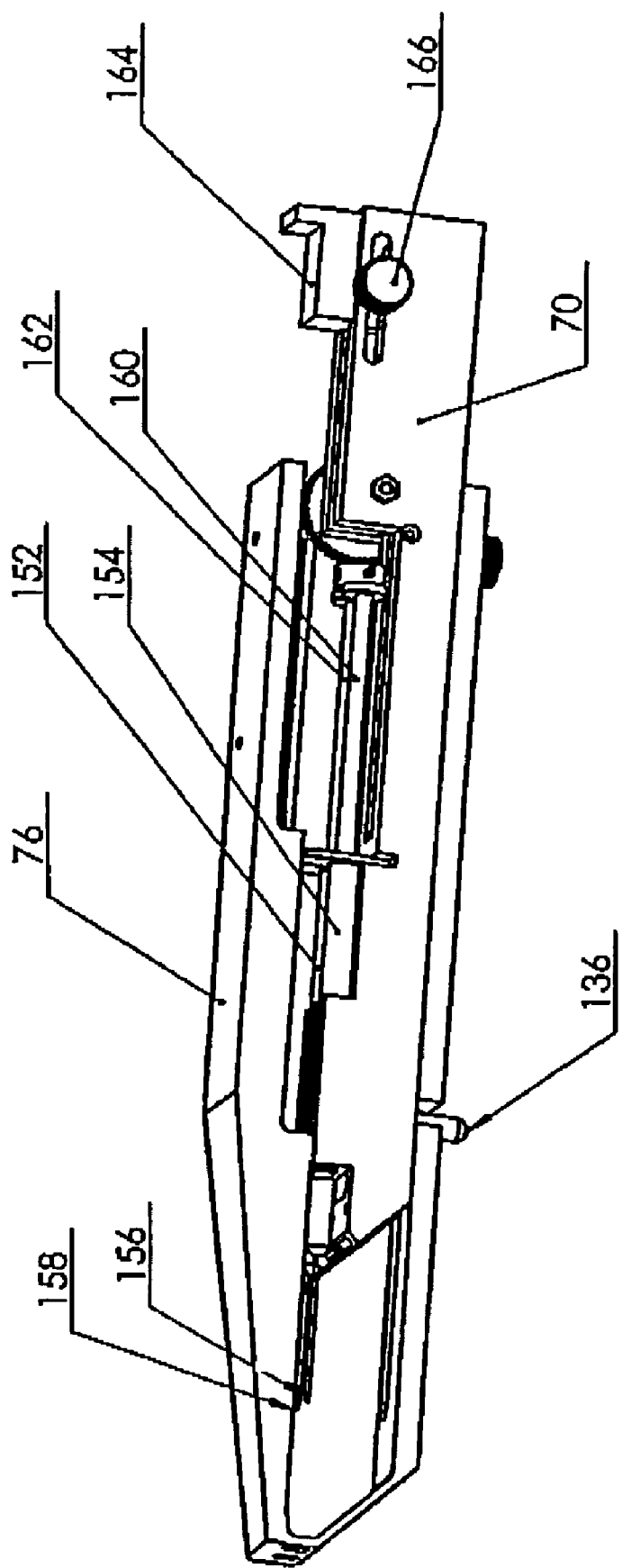
FIG. 14 is a side view of the device of FIG. 7 when fully assembled ready to start the process.

The base 70 is inserted into cover 76 through the open side thereof, the pin 136 in the bottom of base 70 sliding along the groove 132 in a direction perpendicular to the longitudinal extent of the base until it reaches the bend in groove 132. Four adjustments are then made. Firstly, the lever 159 is adjusted so that the needles only stick out of the cover by a distance corresponding to the fat thickness of the subject to be treated (i.e. to the depth of initial needle insertion before fluid injection commences). Next, the base 70 is pushed forward within the cover 76 to reach the maximum desired needle insertion depth and the screw 166 is locked within aperture 122 at this point. The base is then pushed back towards the lever 159 and the further gear-rack mechanism 171 is pushed forward against the syringe pistons ready for injection The device is then ready to start the injection process as shown in FIG. 14.

Figure 15:
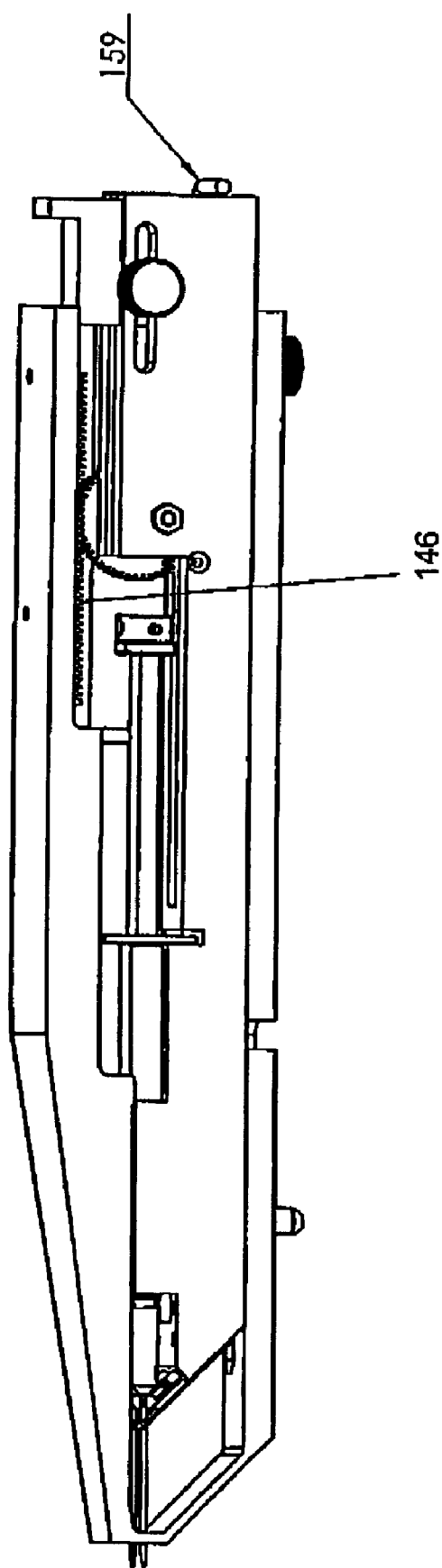
FIG. 15 is a side view of the device of FIG. 7 at the point at which the needles have penetrated the skin, ready to start the injection and needle insertion process.

Next, the flat portion 140 of the cover 76 is placed on the skin of a subject to be treated and the base 70 is moved towards the first end 134 of the cover by pushing the base in that direction using the pin 136. By moving the base 70 forward, the needles are moved towards and then through the apertures 142, 144 in the cover 76 so that they penetrate the skin of the subject to be treated. The device at this position is shown in FIG. 15 and as can be seen, the gear wheel 148 engages toothed track 146.

Figure 16:
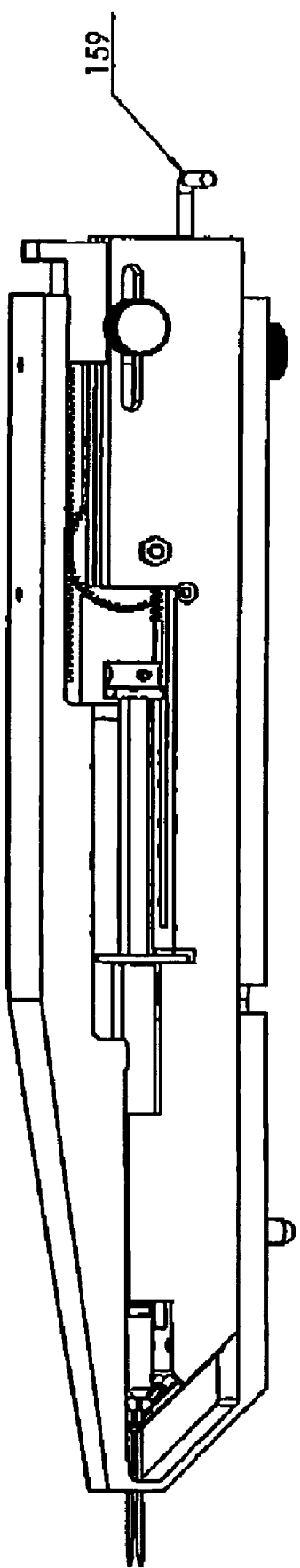
FIG. 16 is a side view of the device of FIG. 7 halfway during needle insertion.
Figure 17:
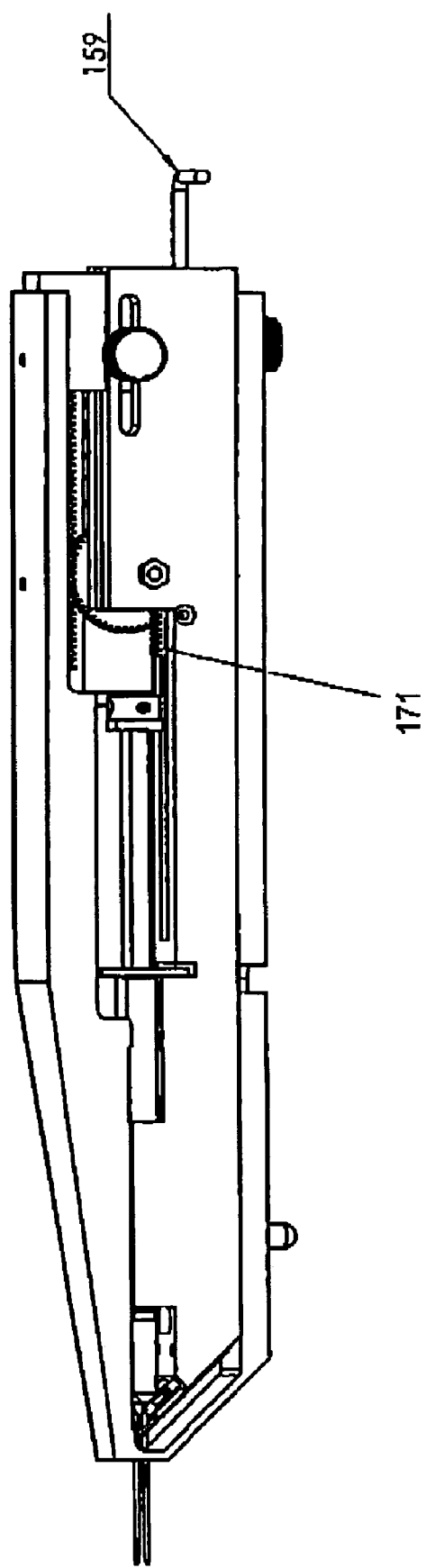
FIG. 17 is a side view of the device of FIG. 7 when needle insertion and injection have been completed (i.e. when the device is ready for electroporation to be carried out, before the needles are withdrawn)

To cause synchronised needle insertion and fluid injection, the pin 136 is then manually pushed further forward in the groove 132 thus moving the cover 76 back towards the stopping member 164 and hence inserting the needles to a depth determined by the relative position of the stopping member while causing gear wheel 148 to rotate. The rotation of gear wheel 148 causes the smaller gear wheel 149 to rotate also thus pushing in the piston rods into the syringes such that fluid is injected gradually through the needles over the depth of insertion of the needles. FIGS. 16 and 17 respectively show the device halfway through needle insertion and when insertion has been completed.

After injection has been completed, an electric field is activated through a current supplied through the needles. The device includes, or is used in conjunction with, a power supply or pulse generator and a control box (not shown) through which the level of the voltage supplied for electroporation can be varied. Further, the amount of current delivered through the needles during electroporation can be measured. Similarly, other characteristics such as electrical resistance can also be measured and recorded either before or after the application of the voltage pulses. The needles are subsequently withdrawn from the subject being treated, by moving pin 136 back in groove 132 to pull the base back from the cover such that the needles are clear of the cover and the base is then removed from the cover through the open side thereof. The needles can then be lifted away from the base and replaced by new syringe devices when a new treatment is required. In an alternative where the device is set up for multiple injections with a multi-dose syringe, the needles are retained in the base and further injections can then be carried out.

In an alternative embodiment of the device, automatic needle insertion and injection can be achieved by respective servo motors. This has the advantage that the depth of needle insertion can be varied using a control for the servo motors.

When treating a human or animal subject, it is important that injection of fluid is commenced and stopped at suitable needle depths. The depths at which injection should be started and stopped will vary from subject to subject depending on the thickness of the superficial fat layer and muscle of the subject. Thus, the device, power supply or control box may include means for measuring the change in impedance between the needles of the two syringes during insertion. This change in impedance provides an indication of when the needles have moved into the desired type of body tissue for fluid injection to commence as the impedance measured between the needles will be different for different types of body tissue. In an alternative embodiment of the device, an ultrasound transducer can be provided on the tip of a needle to measure the depth of the muscle below the tip of the needle and so determine when injection should be commenced.

The device described above could be used with standard syringes as are known in the art. However, it could alternatively be used with prefilled vials or barrels containing the treatment fluid in single or multiple doses and adapted to be connected to injection needles. This has the advantage that the user does not need to fill a syringe with the appropriate dose from a bottle of medicament/solution.

A single-dose barrel could be used for treating humans but a multiple dose barrel could, for example be used to treat a whole herd of farm animals with a single needle.

The syringes or barrels for use with the device according to the invention could be identified by unique bar-codes or other identifiers. The bar-codes could be stored in an electronic controller for the device and could be linked to the patient protocol or animal number. Ideally, an iris-scan or ID tag could be used to identify a patient and a DNA ID code could be provided on the fluid vessel(normally in the form of a bar-code). The patient protocol could be automatically retrieved from a computer when the bar-code on the fluid vessel was read prior to use, leading to great savings in time and effort in clinical situations. Data such as the level of current applied during electroporation, and the amount of DNA or fluid injected could also be stored electronically with the patient protocol. This would enable improved tracking of patient records.

A test of the device of the third embodiment has been carried out on sheep. The device of FIG. 7 was used to distribute DNA encoding SEAP or beta-galactosidase in body tissue. Electroporation was carried out immediately after insertion of the needles and injection. To administer SEAP for measurement in serum, three sheep were sedated and shaved at one side of the rear. Local anaesthetics were applied in a half circle around the site of treatment. The device was loaded with syringes containing DNA encoding human serum alkaline phosphatase (SEAP). One dose consisted of 33 µg DNA in a total of 200 µl. After insertion and injection, current was applied through the needles (400 µsec pulses, 1000 Hz, repeated 7-10 times, 35-60 V/cm). Serum samples were collected 7 days later and measured for SEAP expression by the method described by Chastain in Journal of Pharmaceutical Science 90 474-484 (2001).

To transfect muscle tissue with cDNA encoding beta-galactosidase (β-gal), in order to assess β-gal expression, one sheep was treated as described above. The device was loaded with syringes containing DNA encoding beta-galactosidase, and one dose consisted of 40 µg DNA in a total of 200 µl. Muscle biopsies were taken 3 days later and beta-galactosidase activity was visualised by the method of Sanes et al. Development 113 1181-91 (1991).

The results of the test are shown in FIG. 19 which shows the amount of SEAP in serum and FIGS. 20a and 20b which show the beta-galactosidase in muscle. The sheep were given 3 different doses of DNA encoding SEAP as shown in FIG. 19. As shown in FIGS. 20a and 20b, the method gave even distribution of DNA which in turn gives better and more reproducible accessibility to target cells and thereby better transfection.

As a further test of the third embodiment of the invention, experiments were conducted to measure the resistance between the needles following insertion and optionally injection. Sheep were used for the purpose. The syringes were filled with saline, mounted on the base unit of the device and the cover applied. The needles of the device were inserted into the muscle with or without injection of saline and the resistance measured by use of a control box.

The resistance in muscle without saline injected was measured at 332 ohms, with a total of 100 microliter saline injected the resistance was 291 ohms and resistance in muscle with a total of 400 microliter saline injected was 249 ohms.

In a yet further test, the third embodiment was also tested upon a human volunteer in order to assess whether the use of this device would be tolerable in humans and whether local anaesthesia would be necessary.

The syringes were filled with saline and mounted in the device. The device was pre-set to allow penetration through the skin (3 mm) and a further 1 cm of needle insertion with concomitant injection of saline.

The skin of the leg muscle was disinfected and the needles were inserted into the skin. Then the needles were further inserted, and saline injected, into the muscle by pushing the knob (136). When the needles were in place, the electroporation was performed. The pulse given lasted for 20 ms. The voltage was changed successively from 10 V to 70 V (in 10 V steps), with new insertions and injections of saline each time.

At the highest voltage the current delivered was around 240 mA. The resistance in the muscle tissue was around 300 ohms (within the same range as seen in sheep).

The description from the volunteer was that the injection and insertion were without any pain. The electrical stimulation was rated as unpleasant but not painful. Some stiffness in the treated area was experienced 1-3 hours after the treatment. The stiffness was less pronounced than after physical exercise. No anesthesia was used or considered necessary in this case although a local anesthesia may be beneficial if larger areas of the muscle are to be treated.

The embodiments of the electroporation device described above are preferred embodiments only to which various modifications could be made. For example, the sheaths in the first embodiment could be made of a material other than Teflon and the apertures in them could be provided in a different pattern. Further, although the device has been described as including a syringe arrangement to which the needles are connected, it will be appreciated that this need not be an integral part of the device. Thus, in an alternative embodiment, the needles in the device could be left free to be connectable to a fluid delivery system such as a syringe in use.

Further, although the needles of the device of the second embodiment have been described as being attached to a syringe arrangement, it will be appreciated that the needles and syringe part could be provided separately. Further, although the housing has been described as being formed in two halves each having two recesses formed therein, it will be appreciated that it could be formed by any number of parts which allowed the needles to be removed from the housing without pulling out in the axial direction. Further, it could be adapted to hold any desired number of needles. Thus, the scope of the invention is not limited by the embodiments of the device as described above but rather is defined by the scope of the appended claims.

The invention claimed is:

1. A method for delivering an active agent into a body tissue, comprising:
    injecting a fluid containing an active agent into a body tissue to be treated through a hollow needle while the needle is being inserted into the body tissue; and
    electroporating cells of the body tissue to be treated during or after the fluid has been injected, thereby delivering the active agent into the body tissue.

2. A method as claimed in claim 1, wherein the needle tip is inserted through the skin and injection is then carried out while the needle is inserted further into the body tissue.

3. A method as claimed in claim 1 or 2, wherein the injection is commenced when the needle reaches a first desired depth in the body tissue and is stopped when the needle reaches a second desired depth in the body tissue.

4. A method as claimed in claim 1 or 2, wherein a change in impedance or resistance is used to determine when the needle has reached a desired depth in the body tissue.

5. A method as claimed in claim 3, wherein the depth of the needle in the body tissue is sensed using an ultrasound transducer.

6. A method as claimed in claim 1 or 2 wherein electroporation is effected by applying a voltage to the needle.

7. A method as claimed in claim 1 or 2 wherein the needle is withdrawn from the body tissue, an electrode is inserted in the place of the needle, and a voltage is applied to the electrode.

8. A method as claimed in claim 4 wherein determining when the needle has been inserted to a desired depth in body tissue comprises measuring a change in impedance as the needle is inserted into the body tissue.

9. A method as claimed in claim 8, wherein two needles are inserted into the body tissue adjacent one another and the impedance between the needles is measured.

10. A method as claimed in claim 1, wherein the active agent is a pharmaceutical agent.

11. A method as claimed in claim 1, wherein the active agent is a nucleic acid.

12. A method as claimed in claim 11, wherein the nucleic acid comprises DNA.

* * * * *